(12) United States Patent
Alghazali et al.

(10) Patent No.: US 12,097,304 B2
(45) Date of Patent: *Sep. 24, 2024

(54) BIOCOMPATIBLE STRUCTURE FOR TISSUE REGENERATION AND METHODS OF MAKING AND USING SAME

(71) Applicant: BOARD OF TRUSTEES OF THE UNIVERSITY OF ARKANSAS, Little Rock, AR (US)

(72) Inventors: Karrer M. Alghazali, Little Rock, AR (US); Zeid A. Nima, Little Rock, AR (US); Alexandru S. Biris, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 168 days.

This patent is subject to a terminal disclaimer.

(21) Appl. No.: 15/591,728

(22) Filed: May 10, 2017

(65) Prior Publication Data

US 2018/0326123 A1 Nov. 15, 2018

(51) Int. Cl.
| | |
|---|---|
| *A61L 27/36* | (2006.01) |
| *A61L 27/12* | (2006.01) |
| *A61L 27/14* | (2006.01) |
| *A61L 27/18* | (2006.01) |
| *A61L 27/20* | (2006.01) |
| *A61L 27/38* | (2006.01) |
| *A61L 27/54* | (2006.01) |
| *A61L 27/56* | (2006.01) |
| *A61L 27/58* | (2006.01) |
| *A61K 9/14* | (2006.01) |
| *A61K 31/4453* | (2006.01) |
| *A61K 31/704* | (2006.01) |
| *C07C 211/38* | (2006.01) |
| *C07C 229/36* | (2006.01) |
| *C07D 209/14* | (2006.01) |
| *C07D 209/24* | (2006.01) |
| *C07D 211/22* | (2006.01) |
| *C07D 215/22* | (2006.01) |
| *C07D 265/18* | (2006.01) |
| *C07D 277/56* | (2006.01) |
| *C07D 405/12* | (2006.01) |
| *C07D 473/18* | (2006.01) |
| *C07D 473/30* | (2006.01) |
| *C07D 491/22* | (2006.01) |
| *C07D 501/22* | (2006.01) |
| *C07H 15/252* | (2006.01) |
| *C07H 17/08* | (2006.01) |

(52) U.S. Cl.
CPC ........... *A61L 27/3695* (2013.01); *A61L 27/12* (2013.01); *A61L 27/14* (2013.01); *A61L 27/18* (2013.01); *A61L 27/20* (2013.01); *A61L 27/3608* (2013.01); *A61L 27/38* (2013.01); *A61L 27/54* (2013.01); *A61L 27/56* (2013.01); *A61L 27/58* (2013.01); *A61L 2300/256* (2013.01); *A61L 2300/258* (2013.01); *A61L 2300/414* (2013.01); *A61L 2400/08* (2013.01); *A61L 2400/12* (2013.01); *A61L 2430/02* (2013.01)

(58) Field of Classification Search
CPC ...... A61L 27/3695; A61L 27/12; A61L 27/14; A61L 27/18; A61L 27/20; A61L 27/3608; A61L 27/38; A61L 27/54; A61L 27/56; A61L 27/58; A61L 2300/256; A61L 2300/258; A61L 2300/414; A61L 2400/08; A61L 2400/12; A61L 2430/02; A61L 27/3834
See application file for complete search history.

(56) References Cited

U.S. PATENT DOCUMENTS

| | | | | |
|---|---|---|---|---|
| 8,529,935 | B2* | 9/2013 | Giammona | A61L 27/54 |
| | | | | 514/354 |
| 8,741,318 | B2* | 6/2014 | Biris | A61L 27/54 |
| | | | | 424/602 |
| 8,936,805 | B2* | 1/2015 | Biris | A61F 2/28 |
| | | | | 424/423 |
| 9,005,286 | B2 | 4/2015 | Giorno | |
| 9,107,751 | B2* | 8/2015 | Winterbottom | A61L 27/56 |
| 9,763,788 | B2* | 9/2017 | Biris | A61F 2/28 |
| | | | | 424/423 |

(Continued)

FOREIGN PATENT DOCUMENTS

| | | | | |
|---|---|---|---|---|
| CN | 1429857 A | 7/2003 | | |
| CN | 101874751 A | * 11/2010 | ............. | A61L 27/12 |

(Continued)

OTHER PUBLICATIONS

Yang et al. Journal of Industrial and Engineering Chemistry 33 (2016) 221-225 (Year: 2016).*

(Continued)

*Primary Examiner* — Mina Haghighatian
*Assistant Examiner* — Janice Y Silverman
(74) *Attorney, Agent, or Firm* — Locke Lord LLP; Tim Tingkang Xia, Esq.

(57) ABSTRACT

A method for forming a biocompatible structure includes the steps of forming a layered structure having alternatively disposed first layers and second layers, where the first layers includes at least one polymer and first particles, and the second layers includes second particles; and treating the layered structure with a washing solvent to form the biocompatible structure, where the first particles are solvable in the washing solvent.

13 Claims, 6 Drawing Sheets

(56) References Cited

U.S. PATENT DOCUMENTS

| | | | |
|---|---|---|---|
| 10,238,496 B2* | 3/2019 | Biris | A61F 2/28 424/423 |
| 2007/0061015 A1 | 3/2007 | Jensen et al. | |
| 2007/0212388 A1* | 9/2007 | Patravale | A61L 33/08 424/422 |
| 2012/0288699 A1* | 11/2012 | Ahlberg | A61L 24/00 428/323 |
| 2013/0304229 A1* | 11/2013 | Biris | A61F 2/28 623/23.51 |
| 2015/0238655 A1* | 8/2015 | Jongpaiboonkit | A61K 38/1841 424/602 |
| 2016/0331869 A1 | 11/2016 | Biris | |

FOREIGN PATENT DOCUMENTS

| | | |
|---|---|---|
| EP | 1277450 A2 | 1/2003 |
| WO | 2007103372 A2 | 9/2007 |
| WO | 2014143131 A1 | 9/2014 |

OTHER PUBLICATIONS

Velev, O. and Kaler, E. Adv. Mater. 2000, 12, No. 7, 531-534 (Year: 2000).*

Dreaden et al. Chem Soc Rev. Apr. 7, 2012; 41(7): 2740-2779 (Year: 2012).*

Le Nihouannen et al. Bone 36 (2005) 1086-1093 (Year: 2005).*

Ajdukovic et al. J. Nanosci. Nanotechnol. 2016, vol. 16, No. 2, 1420-1428. (Year: 2016).*

Birgani et al. Acta Biomaterialia 36 (2016) 267-276. (Year: 2016).*

Henkel, Jan et al., "Bone Regeneration Based on Tissue Engineering Conceptions—A 21st Century Perspective", Bone Research, vol. No. 3, pp. 216-248, Accepted: Jul. 20, 2013.

Moreno, M. et al., "Scaffolds for Bone Regeneration: State of the Art", Current Pharmaceutical Design, vol. No. 22, Bentham Science Publishers, pp. 2726-2736, 2016.

Orza, Anamaria et al., "Multistructural biomimetic substrates for controlled cellular differentiation", IOP Publishing, Nanotechnology, vol. No. 25-065102, pp. 1-13, Published: Jan. 16, 2014.

Alghazali, Karrer M. et al., "Bone-tissue engineering: complex tunable structural and biological responses to injury, drug delivery, and cell-based therapies", Taylor & Francis, Drug Metabolism Reviews, vol. No. 47; Issue No. 4, pp. 431-454, Published: Dec. 4, 2015.

Hutmacher, Dietmar W., "Scaffolds in tissue engineering bone and cartilage", Elsevier, Biomaterials, vol. No. 21, pp. 2529-2543, 2000.

Keating, J. F. et al., "Substitutes for Autologous Bone Graft in Orthopaedic Trauma", The Journal of Bone & Joint Surgery, vol. No. 83-B, Issue No. 1, pp. 3-8, Jan. 2001.

Mallick, et al., "Advancement in Scaffolds for Bone Tissue Engineering: A Review", IOSR-JPBS, 2015, pp. 37-54, vol. 10(1).

Sampath et al., "Fabrication of Porous Materials from Natural/Synthetic Biopolymers and Their Composites". Materials, 2016, vol. 9, 991.

Korean Intellectual Property Office, "International Search Report for PCT/US2018/028793", KR, Aug. 8, 2018.

Ghosh, S. et al., "Bi-layered constructs based on poly(L-lactic acid) and starch for tissue engineering of psteochondral defects", Materials Science and Engineering C, Vo. 28, No. 1, 2007, pp. 80-86.

European Property Office, "Supplementary European Report for EP Application No. 18 79 7953", The Hague, Dec. 23, 2020.

CNIPA, "First Office Action for CN Application No. 201880031242.3", China, Jun. 17, 2021.

* cited by examiner

BIOCOMPATIBLE STRUCTURE FOR TISSUE REGENERATION AND METHODS OF MAKING AND USING SAME

STATEMENT AS TO RIGHTS UNDER FEDERALLY-SPONSORED RESEARCH

This invention was made with government support under grant number W81XWH-15-1-0666 awarded by DOD-MRMC. The government has certain rights in the invention.

FIELD

The invention relates generally to a biocompatible structure for tissue regeneration, and more particularly to bone regeneration using multicomponent and multistructural biocompatible scaffold that has a controllable porosity.

BACKGROUND

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

The regeneration medicine has been remarkably developed over a past decade. Such development based on overcoming the drawbacks associated with traditional clinical trials that might causes clinical fail such as immunological rejection, tissue death at the donor site and hazard of promoting infections after implant application, and pain associate with the grafts.

As part of the effort to solve the above described problems, artificial regeneration scaffold could be used instead of traditional autografts, allograft, and xenograft. The scaffold can be fabricated from different material such as natural or synthesis material. However, it is still a challenge to build an artificial scaffold that meets critical requirements for tissue regeneration.

Therefore, a heretofore unaddressed need exists in the art to address the aforementioned deficiencies and inadequacies.

SUMMARY

In one aspect, the present inventions relates to a method for forming a biocompatible and/or biodegradable structure of controllable shape. In certain embodiments, the method includes: forming a layered structure having alternatively disposed first layers and second layers, where the first layers comprises at least one polymer and first particles or mixtures of particles, and the second layers comprises second particles; and treating the layered structure with a washing solvent to form the biocompatible structure, where the first particles are solvable or mixable in the washing solvent.

In certain embodiments, the at least one polymer or combinations of polymers comprise one or more components of chitosan, polylactide (PLA), polyglycolide (PGA), poly(lactide-co-glycolide) (PLGA), poly(e-caprolactone), polydioxanone, polyanhydride, trimethylene carbonate, poly (β-hydroxybutyrate), poly(g-ethyl glutamate), poly(desaminotyrosyl-tyrosine-hexyl ester (DTH) iminocarbonate), poly (bisphenol A iminocarbonate), poly(ortho ester), polycyanoacrylate, polyphosphazene, modified polysaccharides, modified proteins, and polyurethane. The modified polysaccharides comprise cellulose, chitin, or dextran. The modified proteins comprise fibrin, or casein.

In certain embodiments, the first particles comprise sodium chloride crystals, sugar crystals, baking soda crystals, powders, polymers, hydrogels, and/or gels. In certain embodiments, a size of the first particles is in a range of 1 μm-5 mm.

In certain embodiments, a ratio between the first particles and the at least one polymer is in a range of about 0%-99.99999% by weight.

In certain embodiments, the first layers are formed by: dissolving the at least one first polymer in a first solvent to form a first solution, where the first particles are insoluble in the first solvent; forming a polymer film from the first solution, and in certain cases treating the polymer film to obtain polymer powder, mixing the polymer powder, the polymer film, and the first particles to form a first mixture; and distributing the first mixture to form the first layers.

In certain embodiments, a ratio between the at least one first polymer and the first solvent is in a range of 0.0001-99.9999%. In certain embodiments, the first mixture further comprises nano-hydroxyapatite (nHA), hydroxyapatite with sizes from nanometers to millimeters, bone particles with sizes from nanometers to millimeters, demineralized bone particles with sizes from nanometers to millimeters, calcium phosphate powders with sizes from nanometers to millimeters, allografts with sizes from nanometers to millimeters, ceramic particles with sizes from nanometers to millimeters, oxide particles with sizes from nanometers to millimeters and the first solvent.

In certain embodiments, the second particles comprise gold particles, gold nanoparticles, silver particles, silver nanoparticles, cobalt particles, cobalt nanoparticles, graphene, hydroxyapatite particles, nano or micro hydroxyapatite, calcium phosphate particles, calcium phosphate nanoparticles, bone particles, bone nanoparticles, ceramic particles, ceramic nanoparticles, polymer particles, polymer nanoparticles, and/or hydrogels.

In certain embodiments, a ratio between the second layers and the first layers is in a range of about 0-99.999999% by weight.

In certain embodiments, the method further comprising adding an active material to the biocompatible structure, wherein the active material comprises of one or multiple of the following: drugs, growth factors, proteins, antibodies, DNA, RNA, and cells (tissues specific cells, stem cells, etc).

In certain embodiments, the first layers and the second layers are formed by injection, cast deposition, dip coating, deposition, spraying (air spraying), electrospraying, thermal spraying, or three dimensional (3D) printing in order to provide the shape and the size that is desired by the application.

In a further aspect, the present invention relates to a biocompatible structure, formed from a layered structure. In certain embodiments, the layered structure has alternatively disposed first layers and second layers, the first layers comprises at least one polymer and first particles (and in some embodiments also by hydroxyapatite, bone particles, demineralized bone particles, oxides, metal structures, ceramics in sizes from nanometers to millimeters), and the second layers comprises second particles; and the layered structure is washed with a washing solvent to form the biocompatible structure, and the first particles are solvable in the washing solvent.

In certain embodiments, the at least one polymer 112 comprises chitosan, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(desaminotyrosyl-tyrosine-hexyl ester (DTH) iminocarbonate), poly(bisphenol A iminocarbonate), poly(ortho ester), polycyanoacrylate, polyphosphazene, chitosan, modified polysaccharides (cellulose, chitin, dextran), modified proteins (fibrin, casein), and polyurethane.

In certain embodiments, the first particles comprise sodium chloride crystals, sugar crystals, baking soda crystals, powders, polymers, hydrogels, and gels. In certain embodiments, a size of the first particles is in a range of 1 μm-5 mm.

In certain embodiments, a ratio between the first particles and the at least one polymer is in a range of about 0%-99.9999999% by weight.

In certain embodiments, the first layers further comprise nano-hydroxyapatite (nHA) and/or bone particles, demineralized bone particles, oxides, metal structures, ceramics in sizes from nanometers to millimeters, and a first solvent, and the first particles are insoluble in the first solvent.

In certain embodiments, the second particles comprise gold particles, gold nanoparticles, silver particles, silver nanoparticles, cobalt particles, cobalt nanoparticles, graphene, hydroxyapatite particles, nano- or micro-hydroxyapatite, calcium phosphate particles, calcium phosphate nanoparticles, bone particles, bone nanoparticles, ceramic particles, ceramic nanoparticles, polymer particles, polymer nanoparticles, and hydrogels.

In certain embodiments, the biocompatible structure further comprises an active material. The active material comprises drugs, growth factors, and cells.

In certain embodiments, a ratio between the second layers and the first layers is in a range of about 0-99.99999% by weight.

In yet another aspect, the present invention relates to a biocompatible structure. In certain embodiments, the biocompatible structure comprises alternatively disposed first layers and second layers. The first layers comprise channels formed by washing washable particles from the first layers at positions of the washable particles.

These and other aspects of the present invention will become apparent from the following description of the preferred embodiment taken in conjunction with the following drawings, although variations and modifications therein may be effected without departing from the spirit and scope of the novel concepts of the invention.

BRIEF DESCRIPTION OF THE DRAWINGS

The accompanying drawings illustrate one or more embodiments of the disclosure and, together with the written description, serve to explain the principles of the disclosure. The same reference numbers may be used throughout the drawings to refer to the same or like elements in the embodiments.

DETAILED DESCRIPTION

Figure 1A:
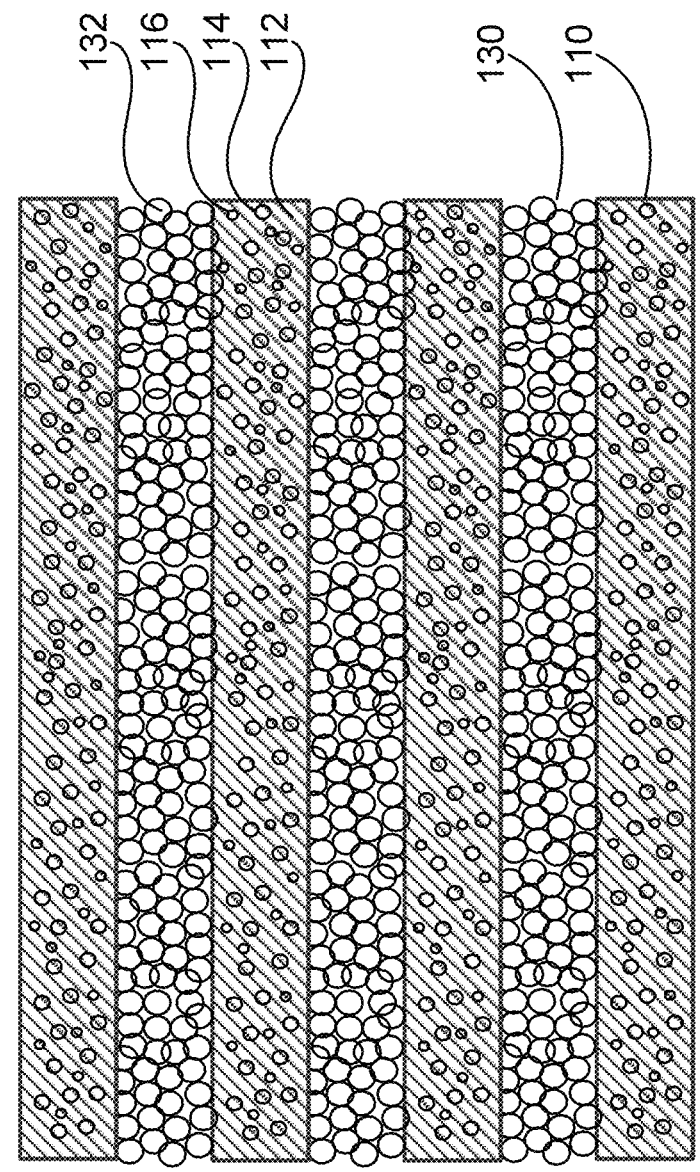
FIGS. 1A and 1B schematically show a biocompatible structure according to one embodiment of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

Typically, "nanoscopic-scale," "nanoscopic," "nanometer-scale," "nanoscale," the "nano-" prefix, and the like refers to elements or articles having widths or diameters of less than about 1 μm, preferably less than about 100 nm in some cases. Specified widths can be smallest width (i.e. a width as specified where, at that location, the article can have a larger width in a different dimension), or largest width (i.e. where, at that location, the article's width is no wider than as specified, but can have a length that is greater), unless pointed out otherwise.

The description will be made as to the embodiments of the present disclosure in conjunction with the accompanying drawings. In accordance with the purposes of this disclosure, as embodied and broadly described herein, this invention, in one aspect, relates to a biocompatible structure that matches with an implant site. The biocompatible structure is biodegradable with a controllable degradation and resorption rate. The controllable degradation and resorption rate match the tissue regeneration process of the implant site. The biocompatible structure has a shape that fits with the infection zone, is configured to totally degradable when the tissue is completely regenerated at the implant site. Further, the biocompatible structure is tunable to become drug delivery systems. Specifically, the biocompatible structure has internal and external structure with a tunable porosity connect by interconnection channels to allow cell migration, diffusion of the nutrition and bodily fluid. In certain embodiments, the three dimensional (3D) biocompatible structure possesses a mechanical strength that matches those at the site of the implantation.

Figure 1B:
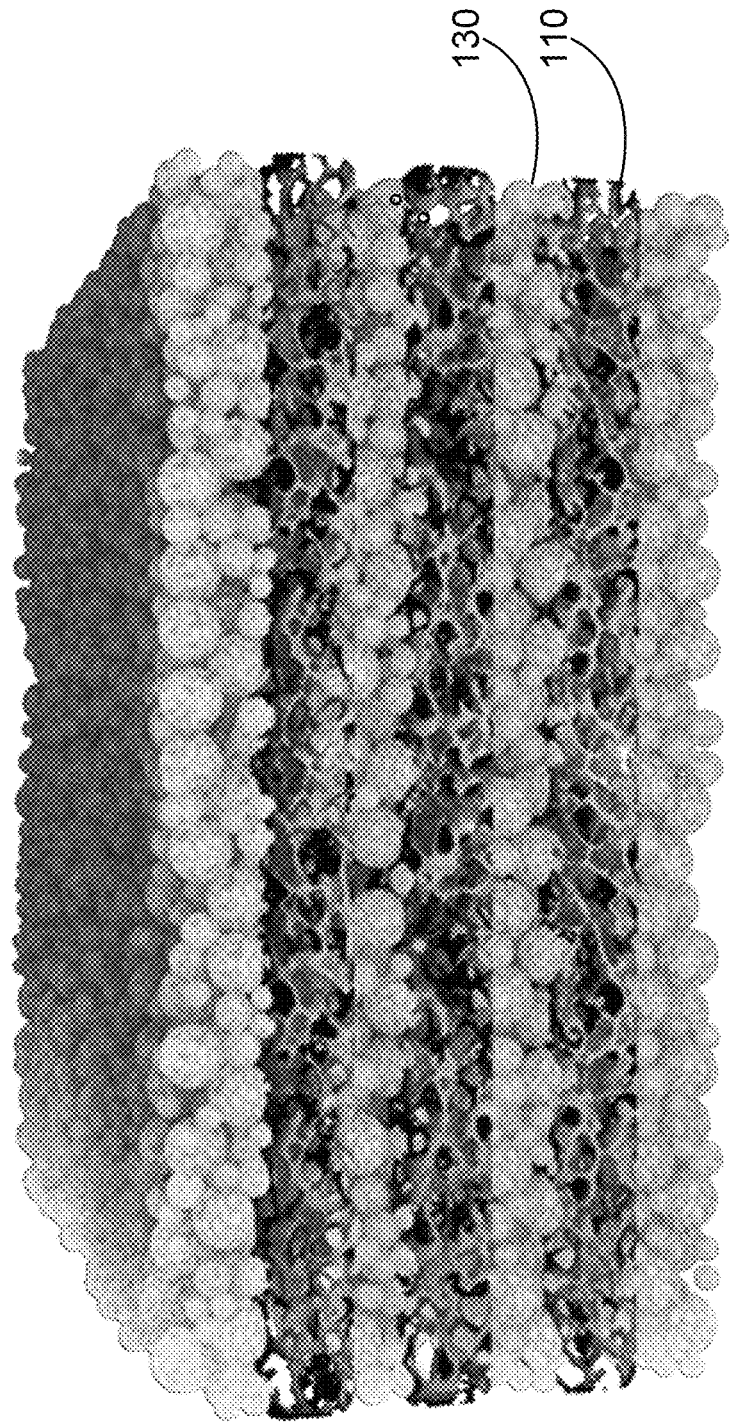

FIGS. 1A and 1B schematically show a biocompatible structure according to certain embodiments of the present invention. The biocompatible structure may be a multidimensional, multicomponent and multishape scaffold that can be used for bone regeneration, or regeneration of other tissues, or regeneration of a combination of different tissues, such as regeneration of both the muscle tissue and the bone tissue in one implant site. The biocompatible structure is built out of a plurality of materials that include one or multiple polymers (biodegradable natural, biocompatible, artificial, etc.), nanomaterials or various materials, bone components (hydroxyapatite in the range of 1000 nm to 10000 μm), nano-sized hydroxyapatite (0.1 nm-5000 nm), calcium phosphate, demineralized bone particles, etc. In certain embodiments, the biocompatible structure is prepared using a layer-by-layer method, and has a major goal of reconstruction of osseous tissue. In certain embodiments, the biocompatible structure is envisioned to support cellular proliferation and differentiation of stem cells into bone cells.

In certain embodiments, the biocompatible structure includes one or a number of various components such as: cells-stem cells (pre- and post-differentiation), tissue specific cells, osteoblasts, osteoclasts, etc.; growth factors to enhance tissue formation, such as bone morphogenetic proteins (BMPs), nerve growth factor (NGF), epidermal growth factor (EGF), etc.; drugs, antimicrobial, anti-inflammatory; and anticancer drugs.

Particles and nanoparticles such as: (gold, silver, Co-nanoparticles, nanorods, nanocubes, nanoplates nanocavities, nanostars, nanopyramids, etc.), graphene, nahohydroxyapatite, hydroxyapatite, calcium phosphate (nano and millimeter sized), bone components (particles and nanoparticles), ceramic particles and nanoparticles, polymers and nanostructures and nanosized polymers, hydrogels.

In certain embodiments, the biocompatible structure is biodegradable with a controllable degradation and resorption. The controllable degradation and resorption match the tissue regeneration process. The biocompatible structure has a shape that fits with the infection zone, is configured to totally degradable when the infected tissue is completely regenerated, and the biocompatible structure is tunable to become drug delivery systems.

In certain embodiments, the biocompatible structure has internal and external structure with a tunable porosity connect by interconnection channels to allow cell migration, diffusion of the nutrition and bodily fluid. In certain embodiments, the 3D biocompatible structure possesses a mechanical strength that matches those at the site of the implantation.

Figure 4:
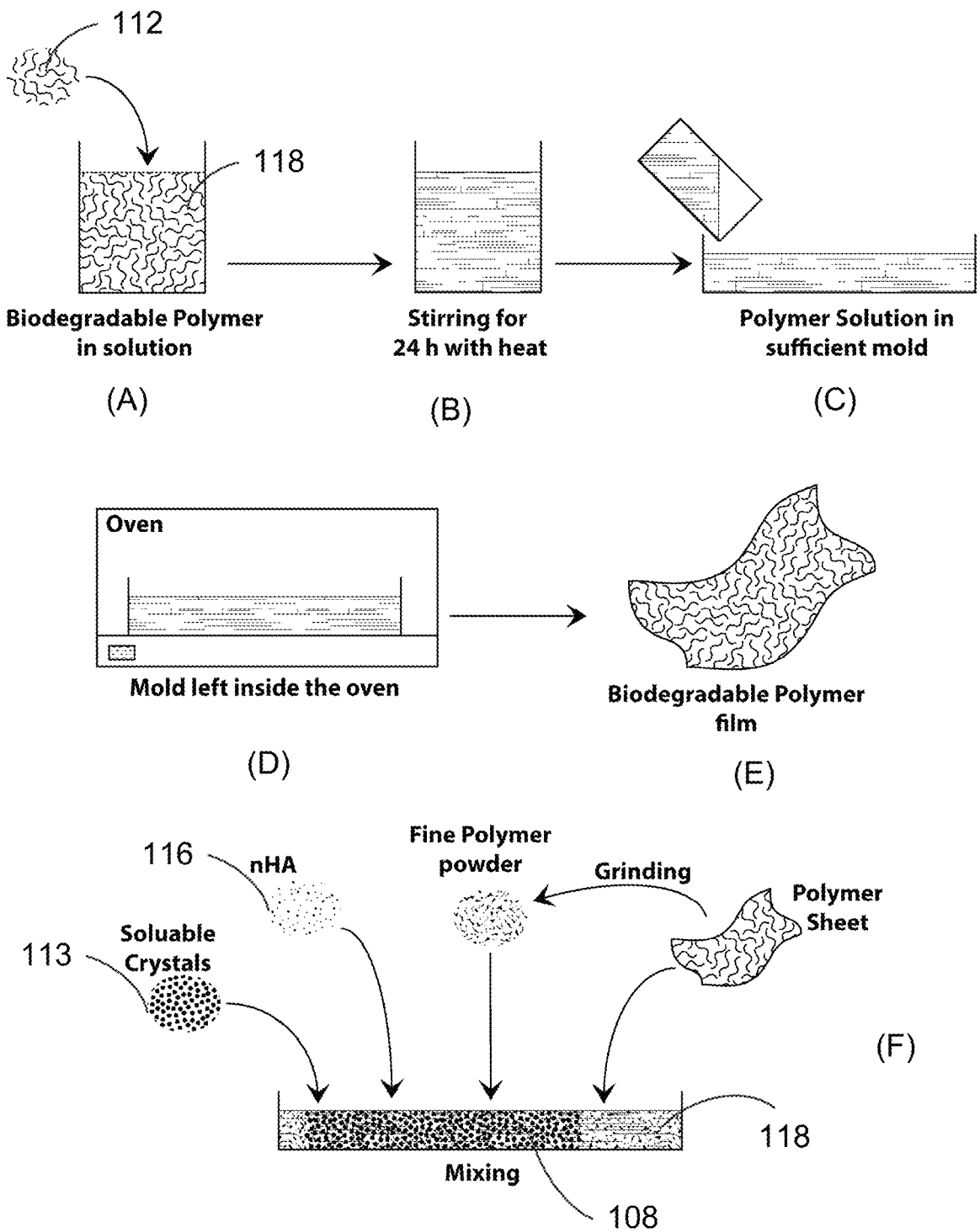
FIG. 4 schematically shows an example of producing a polymer film and a first mixture according to one embodiment of the present invention.
Figure 5:
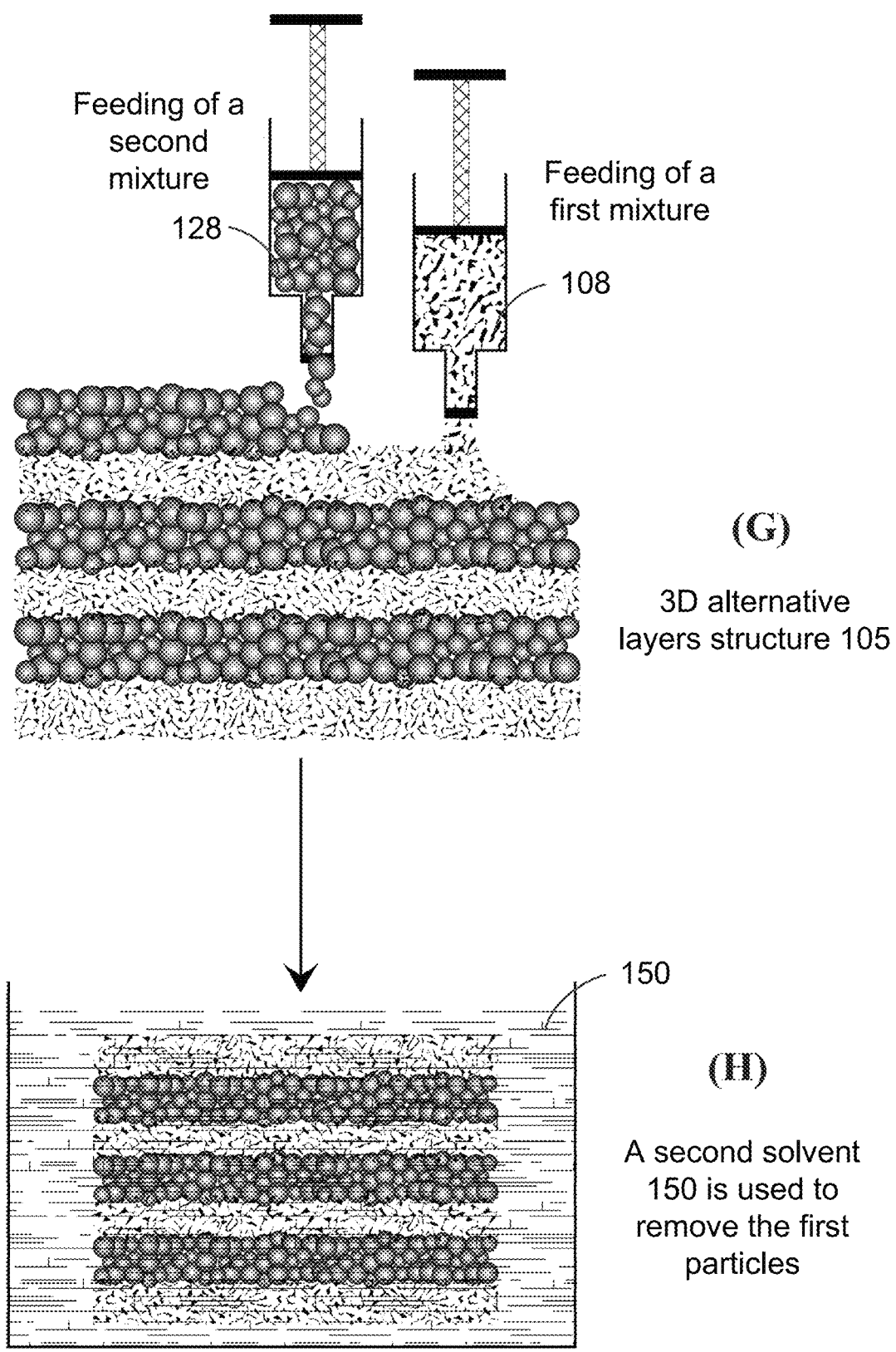
FIG. 5 schematically shows an example of producing a biocompatible structure according to one embodiment of the present invention.

As shown in FIG. 1A, in certain embodiments, a biocompatible structure 100 includes alternatively disposed first layers 110 and second layers 130. The first players 110 comprise at least one polymer 112, and the second layers 130 comprise second particles 132. In certain embodiments, referring to FIG. 5, the biocompatible structure 100 is formed by disposing alternatively layers respectively from a first mixture 108 and a second mixture 128, and then washing the layered structure using a washing solvent 150. In certain cases, if the concentration of the first particles 113 is 0 weight % into polymer 112, the washing step might not be required. Referring to FIGS. 4 and 5, the first mixture 108 includes the at least one polymer 112 and first particles 113, and the second mixture 128 includes the second particles 132. After forming the layers and before the treatment by the washing solvent 150, the first layers 110 contain the at least one polymer 112 and first particles 113. After the treatment by the washing solvent 150, the first particles 113 are partially or completely removed from the first layers 110, leaving voids 114 at the positions of the first particles 113, such that the first layers 110 in the biocompatible structure 100 have a predetermined porosity. The voids 114 may be connected to form channels that have different branches and lengths. The channels may form a network in the first layers 110.

The at least one polymer 112 is composed of a biodegradable, biocompatible polymer or a mixture of polymers that all soluble in a similar solvent, such as a first solvent 118 shown in FIG. 4. The polymer could be a variety of polymers. The ratio between the polymers could vary according to the specifications that include degradation rates, surface energy, and mechanical characteristics. In certain embodiments, a wide range of synthetic biodegradable polymers 112 can be used to form the polymer layer 110, including chitosan, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(desaminotyrosyl-tyrosine-hexyl ester (DTH) iminocarbonate), poly(bisphenol A iminocarbonate), poly(ortho ester), polycyanoacrylate, and polyphosphazene. In certain embodiments, a number of biodegradable polymers derived from natural sources such as chitosan, modified polysaccharides (cellulose, chitin, dextran) or modified proteins (fibrin, casein) can be used to form the polymer layer 110. In one embodiment, the at least one polymer 112 is polyurethane.

The first particles 113 are composed of a material or a mixture of materials that are not soluble in the first solvent 118 of the at least one polymer 112. The material or the material mixture of the first particles 113 includes one or more of: sodium chloride (NaCl) crystals, sugar crystals, baking soda, powders of materials that can dissolve readily in certain solvents, polymers, hydrogels, gels, etc. The first particles 113 is insoluble or have limited solubility in the first solvent 118 of the at least one polymer 112, but is easily soluble in water or a solvent 150 that is different from the solvent of the at least one polymer 112.

In certain embodiments, the ratio between the first particles 113 and the polymer 112 is in a range of about 0% to 100% by weight. In certain embodiments, the first particles 113/the polymer 112 ratio is in a range of about 1% to 80% by weight. In certain embodiments, the first particles 113/the polymer 112 ratio is in a range of about 20% to 60% by weight. In certain embodiments, the first particles 113/the polymer 112 ratio is in a range of about 50% to 100% by weight.

In certain embodiments, the first layers 110 may further include an additive material 116. The addition of the additive material 116 may function to adjust mechanical properties and/or absorption rate of the first layers 110, so as to help the regeneration of tissues in a targeted implant site. In certain embodiments, the additive material includes nano-hydroxyapatite (nHA), bone particles, demineralized bone particles, oxides, metal structures, ceramics in sizes from 1 nm to 100 mm.

In certain embodiments, to form the first mixture 108, a first solvent 118 is used. The polymer 112 is solvable in the first solvent 118, while the first particles 113 are insoluble in the first solvent 118.

The washing solvent 150 is configured to wash off the first particles 113 from the biocompatible structure 100, and it doesn't affect the integrity of other essential components of the biocompatible structure 100. In certain embodiments, the washing solvent is water.

The second particles 132 may include one or more of: particles of gold, silver or Co; nanoparticles of gold, silver or Co, such as in the forms of nanorods, nanocubes, nanoplates, nanocavities, nanostars, nanopyramids, etc; graphene, nanohydroxyapatite; hydroxyapatite; calcium phosphate; bone particles and nanoparticles; ceramic particles and nanoparticles; polymers and nanostructures and nonosized polymers, hydrogels etc.

The biocompatible structure 100 may further include an active material 170. In certain embodiments, the active material 170 includes drugs, such as tissue regeneration enhancement drugs, antimicrobials, anti-inflammatory, cancer-fighting drugs, etc. In certain embodiments, the active material 170 includes growth factors, such as bone morphogenetic proteins (BMPs), nerve growth factor (NGF), epidermal growth factor (EGF), etc. In certain embodiments, the active material 170 includes deoxyribonucleic acid (DNA), ribonucleic acid (RNA), or extracellular matrix proteins, etc. In certain embodiments, the active material 170 includes cells, such as stem cells of various types, tissue specific cells, progenitors, etc. In certain embodiments, the active material 170 includes one or more of the above described molecules or materials, and when the active material 170 includes two or more molecules or materials, the two or more molecules or materials may be independently disposed in the biocompatible structure 100, or may be bonded in advance or in-situ in the biocompatible structure 100.

Based on the properties of the active material 170 and the purpose of applications of the biocompatible structure 100, the active material 170 may be attached to the outer surface of the biocompatible structure 100, may be dispersed all through the active material 170, or only placed in the first layers 110 or the second layers 130.

As shown in FIGS. 1A and 1B, the biocompatible structure 100 may starts from a first layer 110 or a second layer 130, and may ends with a first layer 110 or a second layer 130. In other words, either a first layer 110 or a second layer 130 can be placed at the top or the bottom of the biocompatible structure 100.

In certain aspects, the present invention relates to a novel method to construct a multimensional, multicomponent and multishape biocompatible structure 100 that can be used for bone regeneration. In certain embodiments, the method includes the step of preparing a first mixture 108 for forming the first layers 110 and a second mixture 128 for forming the second layers 130, constructing the layered structure 105 by disposing alternatively the first layers 110 and the second layers 130, and washing the layered structure 105 using the washing solvent 150 to form the biocompatible structure 100. The washing treatment forms voids or channel networks in the biocompatible structure 100.

Figure 2:
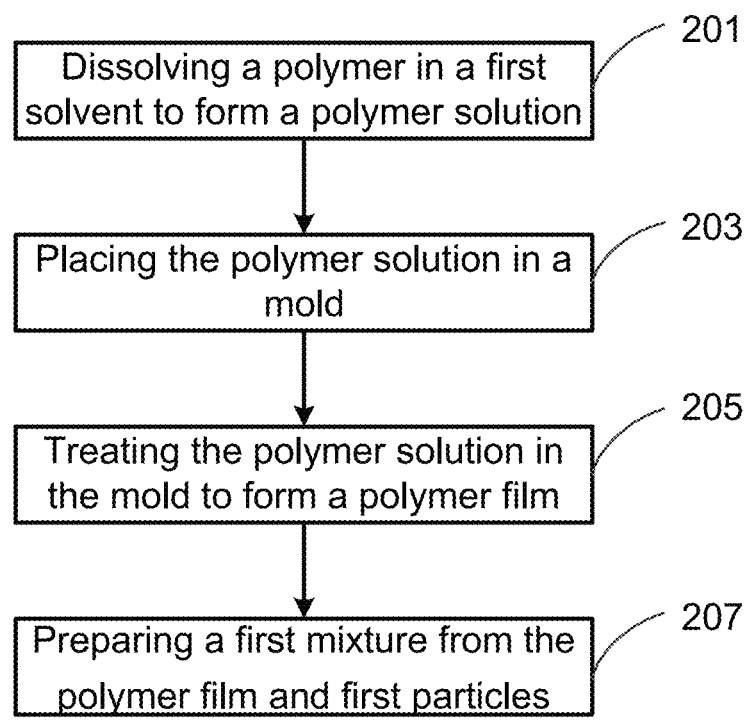
FIG. 2 schematically shows a procedure for producing a polymer film and a first mixture according to one embodiment of the present invention.

FIG. 2 schematically shows a process of preparing a polymer film and a first mixture according to certain embodiments of the present invention. As shown in FIG. 2, at procedure 201, the at least one polymer 112 is dissolved in the first solvent 118 to form a polymer solution. In one example, the polymer 112 is added to the first solvent 118 to form a mixture; and them, in order to speed up the dissolving process, the mixture may be stirred and heated. After stirring under heated condition for a period of time, the polymer 112 is completely dissolved and evenly distributed in the first solvent 118 to form the polymer solution.

At procedure 203, a specific amount of the polymer solution is decanted into a mold. The shape and size of the mold is configured based on the size of the polymer film to be manufactured. In certain embodiments, the mixing of the polymer 112 with the first solvent 118 may be performed in the mold, such that the process of decanting the polymer solution to the mold is not necessary.

At procedure 205, the mold containing the polymer solution is treated to form a polymer film. In certain embodiments, to obtain the polymer film, the mold containing the polymer solution is placed in an oven at a heated temperature for a period of time to form the biodegradable polymer film. In certain embodiments, the oven may be ventilated to dry the polymer film efficiently. In certain embodiments, a large polymer film is produced first, and then cut into strips for further usage.

In certain embodiments, the fluidity or the flowability of the polymer solution is controlled by the ratio between the polymer 112 and the first solvent 118. In one example, 8 gram of polymer 112 is dissolved in 100 ml of the first solvent 118 to obtain an 8% polymer solution. In certain embodiments, the ratio between the first polymer 112 and the first solvent 118 may vary from 0.0001 to 99.9999% by weight. In certain embodiments, the first polymer 112/the first solvent 118 ratio may be in a range of 0.1%-99% by weight (grams per 100 ml). In certain embodiments, the first polymer 112/first solvent 118 ratio may be in a range of 0%-99% by weight. In certain embodiments, the first polymer 112/the first solvent 118 ratio may be about 0-99% by weight, preferably around 8-10% by weight.

In certain embodiments, to increase the homogeneity of the polymer, the polymer film prepared as described above may be powdered and re-solubilized. In certain embodiments, after preparation, the polymer film may contain certain amount of the first solvent 118, may contain a trace amount of the first solvent 118, or may be devoid of the first solvent 118.

After preparing the polymer film, at procedure 207, the first mixture 108 is prepared from the polymer film and the first particles 113. The first mixture 108 can be used later to form the first layers 110. The polymer film 113 may be used directly to form the first mixture 108 after being plasticized or liquidized for example by heating. In certain embodiments, the polymer film 113 is ground to form fine polymer powders before forming the first mixture 108. In certain embodiments, both the polymer film and the polymer powders are used to form the first mixture 108. Before manufacturing the first mixture 108, the first particles 113 may be prepared by grinding into fine particles. The ground particles may be selected using size separation techniques, such as sieving, size selection, etc., to obtain a desired size of the first particles 113. The obtained first particles 113 may have a size from 1 nm to 5 mm. In certain embodiments, the average size of the first particles 113 is in a range of from 1 nm to 5 mm. The size of the first particles 113 may be altered based on the application of the biocompatible structure 100. The first solvent 118 must be inert toward the selective first particles 113. In certain embodiments, the first particles 113 are crystals. In certain embodiments, the additive material 116 may also be used to prepare the first mixture.

In certain embodiments, the first particles 113, the additive materials such as nano-hydroxyapatite (nHA) (or bone particles, demineralized bone particles, oxides, metal structures, ceramics in sizes from nm to mm) 116, the polymer film, the fine polymer powder etc. are all mixed with the first solvent 118 to obtain the first mixture 108. Specifically, a specific amount of the first particles 113 is added to the liquefied biodegradable polymer and mixed with the plasticized biodegradable polymer film. The amount of the first particles 113 controls the internal and external structure, porosity ratio as well as the degradation ratio. For example, by adding 20 gram of the first particles 113, such as soluble crystals, to 1 gram of polyurethane, the porosity ratio of the first layers 110 would be more than 95% (of volume voids) after washing of the soluble crystal 113. In certain embodiments, the ratio between the first particles 113 and the polymer 112 is in a range of about 0% to 100% by weight. In certain embodiments, the first particles 113/the polymer 112 ratio is in a range of about 0% to 99.9999% by weight. In certain embodiments, the first particles 113/the polymer 112 ratio is in a range of about 0% to 99.999% by weight. In certain embodiments, the first particles 113/the polymer 112 ratio is around 50% by weight. As described above, the components of the first mixture 108 may be varied according to the applications, and includes the first particles 113 and at least one of the film or powder of the polymer 112, and optionally at least one of the additive material 116 and the first solvent 118. In one example, the first mixture 108 is formed from the film of the polymer 112, the powder of the polymer 112, the first particles 113, the additive material 116, that are mixed in the first solvent 118.

Figure 3:
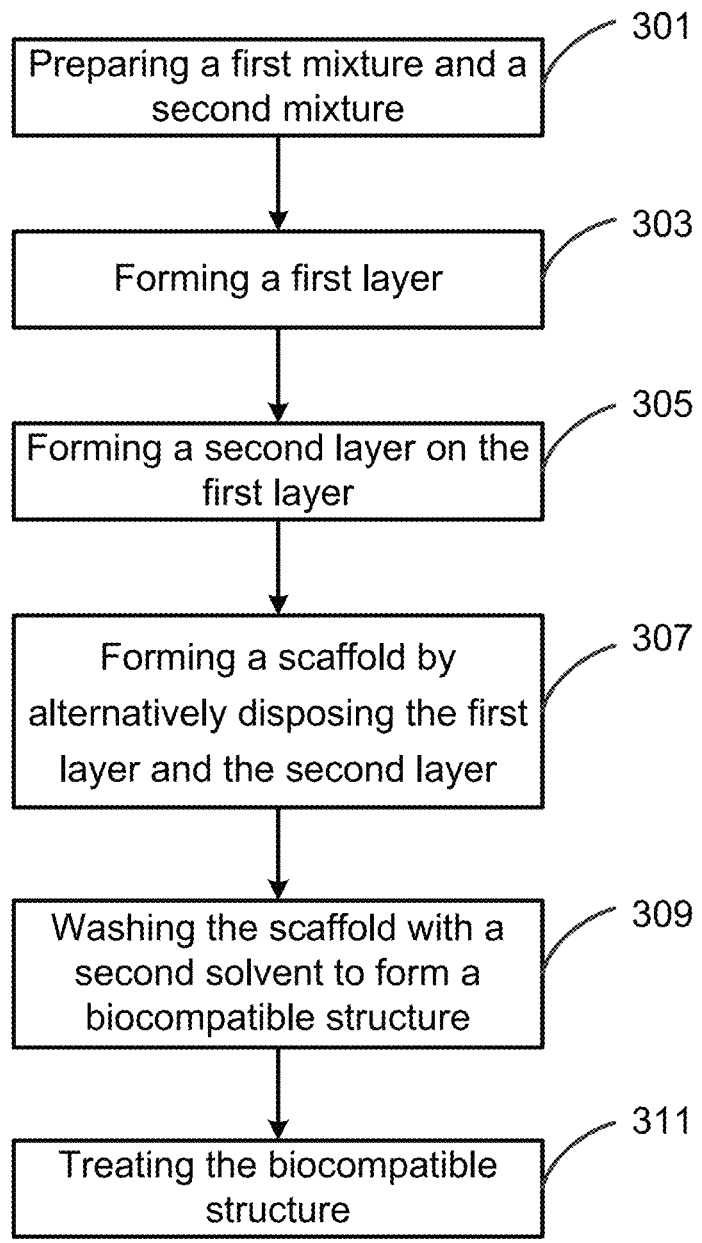
FIG. 3 schematically shows a procedure for producing a biocompatible structure according to one embodiment of the present invention.

FIG. 3 schematically shows a layer-by-layer process for forming a biocompatible structure according to certain embodiments of the present invention. During this process, the first mixture 108 is mixed with the second mixture 128 based on the desired properties of the biocompatible structure 100. As described above, the first mixture 108 contains the polymer 112 and the first particles 113, and optionally the additives such as nHA (bone particles, demineralized bone particles, oxides, metal structures, ceramics in sizes from nm to mm) 116 and the first solvent 118. The second mixture or material 128 contains the second particles 132, and the second particles 132 may include at least one of nanosized hydroxyapatite, bone particles, and bone nanoparticles.

At procedure 301, a first mixture 108 and a second mixture 128 are respectively prepared. The first mixture 108 may be prepared according to the procedure 207 as shown in FIG. 2, which may involve adding and mixing a specific amount of additive material such as nHA 116 (size 1 nm to 500 nm) (bone particles, demineralized bone particles, oxides, metal structures, ceramics in sizes from nm to mm) in the first mixture 108. The weight/weight ratio between the polymer 112 and the nHA (bone particles, demineralized bone particles, oxides, metal structures, ceramics in sizes from nm to mm) 116 in the first mixture 108 is in a range of 100/0 to 0/100 (weight ratio between the polymer 112 and the nHA 116). In certain embodiments, the weight ratio of polymer 112/nHA (bone particles, demineralized bone particles, oxides, metal structures, ceramics in sizes from nm to mm) 116 is about 80/20. After well mixing, the first mixture 108, which is a liquid mixture, may be transferred to a deposition device. The deposition device includes, but is not limited to, an injection device, a spraying device such as an air spraying device or an electrospraying device, a thermal spraying device, or a 3D printer. The next step is the development of uniform deposition patterns.

At procedure 303, a first layer 110 is deposited using the first mixture 108 that may be in a liquid form or a partially liquid form.

At procedure 305, a second layer 130 is formed by depositing a specific amount the second mixture 128 on the first layer 110. The second mixture 128 may include the second particles 132.

By repeating the procedure 303 and 305, that is, by alternatively disposing the first layer 110 and the second layer 130 at procedure 307, a scaffold 105 of the biocompatible structure 100 is manufactured.

At procedure 309, the scaffold 105 is washed with a second solvent 150. The first particles 113 are soluble in the second solvent 150. By washing the first particles 113 out of the first layer 110, void spaces are presented, such that the porosity of the first layer 110 is high.

Further, the method 300 may optionally include a procedure 311 to treat the biocompatible structure. In certain embodiments, the treatment includes adding active molecules 170 to the biocompatible structure 100. In certain embodiments, the treatment includes plasma treating the manufactured biocompatible structure 100. In certain embodiments, the treatment includes modifying the biocompatible structure 100 by adding certain active groups on the biocompatible structure 100.

It should be particularly noted that, unless otherwise stated in the present disclosure, the steps of the method may be arranged in a different sequential order, and are thus not limited to the sequential order as shown in FIG. 3. For example, the layered structure may be built from the procedure 305 instead of procedure 303, such that the first layer is the layer 130 instead of the layer 110.

In another aspect, the present invention relates to an implant having one or more of the biocompatible structures 100 so that the implant has a shape and size matching an implant site. The one or more biocompatible structures 100 forming the implant may have the same or different structure and properties. For example, the implant may have one portion corresponding to a muscle tissue of the implant site and the other portion corresponding to a bone tissue of the implant site. The one portion corresponding to the muscle tissue may have a higher porosity and faster degradation rate that matches the regeneration of the muscle tissue, and may have certain cells or growth factors to promote the regeneration of the muscle tissue. The other portion corresponding to the bone tissue may have a lower porosity and slower degradation rate that matches the regeneration of the bone tissue, and may have certain cells or growth factors to promote the regeneration of the bone tissue.

In a further aspect, the present invention relates to methods of forming an implant. The implant may be formed by combining two or more biocompatible structures 100 as described above.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

Example 1

Preparation of a Polymer Film and a First Mixture

FIG. 4 schematically shows a process of preparing a polymer film and a first mixture according to certain embodiments of the present invention.

As shown in FIG. 4, at procedure (A), a biodegradable polymer 112 is added to a first solvent 118. Then at procedure (B) the mixture of the polymer 112 and the first solvent 118 is stirred for 24 hours under heated condition to improve and speed up the dissolving process, so as to form a polymer solution.

After that, at procedure (C) the polymer solution is decanted to a mold that has sufficient volume and predetermined dimensions, so as to obtain a polymer film having predetermined sizes.

At procedure (D), the mold is placed in an oven and incubated at a heated temperature for a period of time.

At procedure (E), a biodegradable polymer film is obtained, where the first solvent 118 is completely evaporated, or the polymer film may contain a trace amount of the first solvent 118. The obtained polymer film can be used to prepare the first mixture in different ways. In this example, in one hand, the polymer film or the polymer sheet may be liquefied or plasticized; in the other hand, the polymer film may be ground to make fine polymer powder. At least one of the liquefied/plasticized polymer and the polymer powder may be used to form the first mixture, or both the liquefied/plasticized polymer and the polymer powder are used in procedure (F). As shown in procedure (F), at least one of the liquefied film and/or the fine powder of the polymer 112 and the soluble crystals 113 are mixed together. In certain embodiments, nHA 116 or other type of additive material (bone particles, demineralized bone particles, oxides, metal structures, ceramics in sizes from nm to mm) may be further added to the first mixture 108. In certain embodiments, the first solvent 118 is added to the first mixture 108 so that the different components in the first mixture 108 may be mixed thoroughly. In certain embodiments, the liquefied polymer film may be disposed layer by layer in the mixing container, and the crystals 113, the nHA (or bone particles, demineralized bone particles, oxides, metal structures, ceramics in sizes from nm to mm) 116, and the fine polymer power can be disposed between those layers of liquefied polymer films.

In certain embodiments, the fluidity or the flowability of the polymer solution is controlled by the ratio between the polymer 112 and the first solvent 118. In one example, 8 gram of the polymer 112 is dissolved in 100 ml of the first solvent 118 to obtain an 8% polymer solution. In certain embodiments, the ratio between the first polymer 112 and the first solvent 118 may vary from 0.0001 to 99.9999%.

In certain embodiments, to increase the homogeneity of the polymer 112, the polymer film prepared as described above may be powdered and re-solubilized as shown in (F) of FIG. 4. In certain embodiments, after preparation, the polymer film may contain certain amount of the first solvent 118, may contain a trace amount of the first solvent 118, or may be devoid of the first solvent 118.

The first particles 113 may be prepared by grinding into fine particles. The ground particles may be selected using size separation techniques, such as sieving, size selection, etc., to obtain a desired size of the first particles 113. The obtained first particles 113 may have a size from 1 nm to 5 mm. In certain embodiments, the average size of the first particles 113 is in a range of from 1 µm to 550 µm. The size of the first particles 113 may be altered based on the application of the biocompatible structure 100. The first solvent 118 must be inert toward the selective first particles 113. In certain embodiments, the first particles 113 are crystals.

In certain embodiments, the amount of the first particles 113 controls the internal and external structure, porosity ratio as well as the degradation ratio. For example, by adding 20 gram of the first particles 113, such as soluble crystals, to 1 gram of polyurethane, the porosity ratio of the first layers would be more than 95% after washing of the soluble crystal. In certain embodiments, the ratio between the first particles 113 and the polymer is in a range of about 0% to 100% by weight.

Example 2

Preparation of a Biocompatible Structure

FIG. 5 schematically shows a layer-by-layer process for forming a biocompatible structure according to certain embodiments of the present invention. During this process, the first mixture 108 is mixed with the second mixture 128 base on the desired properties. As described above, the first mixture 108 contains the polymer 112 and the first particles 113, and optionally the nHA (bone particles, demineralized bone particles, oxides, metal structures, ceramics in sizes from nm to mm) 116 and the first solvent 118. The second mixture or the second material 128 contains the second particles 132.

In one example, the second particles 132 may include at least one of nanosized hydroxyapatite, bone particles, and bone nanoparticles. This example involves adding and mixing a specific amount of nHA (bone particles, demineralized bone particles, oxides, metal structures, ceramics in sizes from nm to mm) 116 to the first mixture 108 as described in Example 1, and the weight/weight ratio between the polymer 112 and the nHA (or bone particles, demineralized bone particles, oxides, metal structures, ceramics in sizes from nm to mm) 116 in the first mixture is in a range of 100/0 to 0.0010/99.999 (weight of polymer 112/nHA 116). In certain embodiments, the weight ratio of polymer 112/nHA 116 is about 80/20. After well mixing, the first mixture, which is a liquid mixture, may be transferred to a deposition device. The deposition device includes, but is not limited to, an injection device, a spraying device such as an air spraying device or an electrospraying device, a thermal spraying device, or a 3D printer. The next step is the development of uniform deposition patterns.

At procedure (G), a first layer 110 is deposited using the first mixture 108 that is in a liquid form. The deposited first layer 110 has a specific size and shape depending upon the applications. In certain embodiments, the first layer 110 has a thickness from 1 nm to 10 cm, preferably between 250 nm to 1 millimeter. The deposition can be done in a mold with the desired shape or size. The deposition can be done by electrospraying, 3D printing, air-spraying, pouring on a surface etc.

Then the second mixture 128 is disposed on the first layer 110 to obtain a second layer 130 on the first layer 110. The second mixture 128 may include particles of hydroxyapatite, demineralized bone particles, calcium phosphate (CaP), grinded bone, oxides, metals structures, ceramics, etc. with a size between 10 nm to 10 mm, preferably between 0.250 to 20 mm.

By overlaying the second mixture 128 (which may be bone particles) over the first layer 110 of the first mixture 108 to form the second layer 130, then applying another layer of the first mixture 108, and repeating this process, a 3D structure 105 is built till the desire size and height achieved. The amount of the second particles 132 (or bone particles) added to the 3D structure is based on (w/w) ratio with the first mixture 108 (polymer/nHA or bone particles, demineralized bone particles, oxides, metal structures, ceramics in sizes from nm to mm etc). This ratio could be altering based on the application and the desired properties from 0 to 99.9999999%, preferably from 0 to 60%).

Then at procedure (H), the first particles 113 (which may be soluble crystals) are removed from the 3D structure 105 by immersing it into the specific washing solvent 150 for a period of time. The second solvent 150 is able to dissolve the soluble crystal 113 but doesn't affect the integrity of essential component of the 3D structure 105, i.e., the polymer 112, the nHA 116, and bone particles 132. In certain embodiments, optional orbital shaking facilitates the process of removing the soluble crystal 113, also changing the washing solvent 150 with fresh in between the shaking process could also facilitate the removing process.

After completely removing the soluble first particles 113, the 3D structure may be transferred to dry environmental in order to remove the washing solvent 150 (by drying, evaporation, vacuum or heat). The removal of the washing solvent 150 might be carried out at a desire temperature from about room temperature to about 75° C. In certain embodiments, the temperature is about 30-40° C. The removal of the washing solvent 150 can be done inside vacuum condition or non-vacuum condition. Those different treatments might alter the porosity, extension, and the water absorption ability of the obtained biocompatible structure 100. In this example, both the bottom layer (or start layer) and the top layer is the first layer 110. In other embodiments, each of the bottom layer and the top layer may also be the second layer 130. The total number of layers can vary from 1 to a number that would result in the size, shape, and the dimensions desired.

In certain embodiments, the biocompatible structure 100 (or 3D structure) may further be treated with a plasma discharge (oxygen, nitrogen, or other gases and mixtures) to create functional sites, these functional sites could be used to physically or chemically link to one or combination of the tissue regeneration enhancement drugs. Different kind tissue regeneration enhancement drugs could be loaded (antimicrobials, anti-inflammatory). Other active molecules that can be added to the biocompatible structure may include growth factors for example BMP, NGF, EGF, etc, DNA, RNA, extracellular matrix proteins, etc.

The scaffolds can be loaded with drugs, growth factors separately or together and the order is drugs-growth factors or growth factors-drugs. The concentrations can be varied to have biological and medical relevance.

Cells including stem cells of various types, tissue specific cells, progenitors, etc. could be loaded and incorporate within the 3D biocompatible structure 100. The biocompatible structure is envisioned to differentiate the stem cells into bone cells. The biocompatible structure could include other biological components that are part of the bone structure.

In another embodiment of the invention, the scaffold includes drugs that are used to fight cancer and other medical conditions (such as Cosmegen (Dactinomycin), Abitrexate (Methotrexate), Denosumab, Xgeva (Denosumab), Folex (Methotrexate), Folex PFS (Methotrexate), Dactinomycin, Methotrexate, Methotrexate LPF (Methotrexate), Mexate (Methotrexate), Doxorubicin Hydrochloride, Mexate-AQ (Methotrexate, Emplicity (Elotuzumab))) in clinically viable concentrations.

The bonding of the biologically active molecules, such as drugs, growth factors, etc., can be done by physical adsorption, covalent bonding, ionic bonding, Van der Waals forces, hydrogen bonding and they can be deposited by pipetting, spraying, electrospraying, air spraying, during manufacturing, or before use in the operating room or medical facility.

The biocompatible structure or scaffold can be used in conjunction with electromagnetic excitation that could include but not limited to: lasers, radio-frequency (RF), sonic waves, radio waves, ultrasound, etc.

The biocompatible structure 100 according to certain embodiments of the present invention, among other things, has beneficial advantages as follows:
1. The biocompatible structure has a controllable porosity. The porosity is tunable to meet the requirements of regeneration of both soft tissue and hard tissue.
2. The biocompatible is easy to load with drugs or other bioactive molecules.
3. The surface chemistry of the biocompatible is easily modified.
4. The washing of the washable material (first particles) makes the biocompatible structure to have controlled size of void spaces, and the distribution of the void spaces can be easily controlled by mixing and evenly distributing the washable material in the first mixture.
5. The selective washing of the washable material also helps to improve the packing of the biocompatible structure.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

Some references, which may include patents, patent applications, and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LISTING OF REFERENCES

1. Henkel, J.; Woodruff, M. A.; Epari, D. R.; Steck, R.; Glatt, V.; Dickinson, I. C.; Choong, P. F.; Schuetz, M. A.; Hutmacher, D. W., Bone Regeneration Based on Tissue Engineering Conceptions—A 21st Century Perspective. Bone research 2013, 1 (3), 216-48.
2. Moreno, M.; Amaral, M. H.; Lobo, J. M.; Silva, A. C., Scaffolds for Bone Regeneration: State of the Art. Current pharmaceutical design 2016, 22 (18), 2726-36.
3. Anamaria, I. O.; Carmen, M.; Olga, S.; Mircea, D.; Adrian, F.; Horea, M.; Stefana, B.; Thilak, M.; Ganesh, K. K.; Alexandru, S. B., Multistructural biomimetic substrates for controlled cellular differentiation. Nanotechnology 2014, 25 (6), 065102.
4. Alghazali, K. M.; Nima, Z. A.; Hamzah, R. N.; Dhar, M. S.; Anderson, D. E.; Biris, A. S., Bone-tissue engineering: complex tunable structural and biological responses to injury, drug delivery, and cell-based therapies. Drug metabolism reviews 2015, 47 (4), 431-454.
5. Hutmacher, D. W., Scaffolds in tissue engineering bone and cartilage. Biomaterials 2000, 21 (24), 2529-2543.
6. Keating, J. F.; McQueen, M. M., Substitutes for autologous bone graft in orthopaedic trauma. The Journal of bone and joint surgery. British volume 2001, 83 (1), 3-8.
7. Jensen, P.; Biris, A. S., System and method for tissue generation and bone regeneration. Google Patents: 2013.

What is claimed is:

1. A method of forming a biocompatible structure of controllable shape, comprising:
    forming a layered structure having alternatively disposed first layers and second layers, wherein each of the first layers comprises at least one polymer and first particles, and each of the second layers comprises second particles, wherein the first particles are solvable in a washing solvent; and
    treating the layered structure with the washing solvent to solve the first particles in the washing solvent, thereby removing the first particles from the layered structure and forming porosity at positions of the first particles therein, so as to form the biocompatible structure comprising the treated layered structure having the treated first layers of the at least one polymer and the porosity and the treated second layers of the second particles alternatively deposed on each other;
    wherein the second particles comprise hydrogels; and
    wherein the first layers are formed by:
        dissolving the at least one polymer in a first solvent to form a first solution;
        forming a polymer film from the first solution, heating the polymer film, and/or grinding the polymer film to obtain a polymer powder;
        mixing the liquefied or plasticized polymer and/or the polymer powder and the first particles in the first solvent to form a first mixture, wherein the first particles are insoluble in the first solvent, and wherein the first particles are evenly distributed in the first mixture; and
        distributing the first mixture to form the first layers.

2. The method of claim 1, wherein the at least one polymer comprises at least one of chitosan, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(desaminotyrosyl-tyrosine-hexyl ester (DTH) iminocarbonate), poly(bisphenol A iminocarbonate), poly(ortho ester), polycyanoacrylate, polyphosphazene, modified polysaccharides, modified proteins, and polyurethane.

3. The method of claim 1, wherein the first particles comprise sodium chloride crystals, sugar crystals, or baking soda crystals.

4. The method of claim 1, wherein the first mixture further comprises at least one of hydroxyapatite with sizes from 1 nm to 100 mm, bone particles with sizes from 1 nm to 100 mm, calcium phosphate powders with sizes from 1 nm to 100 mm, allografts with sizes from 1 nm to 100 mm, and ceramic particles with sizes from 1 nm to 100 mm.

5. The method of claim 1, further comprising adding an active material to the biocompatible structure, wherein the active material comprises drugs, and/or cells.

6. The method of claim 1, wherein the first layers and the second layers are formed by injection, cast deposition, dip coating, deposition, spraying, electrospraying, thermal spraying, or three dimensional (3D) printing in order to provide desired shapes and sizes.

7. A biocompatible structure formed according to the method of claim 1.

8. The biocompatible structure of claim 7, wherein the at least one polymer comprises at least one of chitosan, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(desaminotyrosyl-tyrosine-hexyl ester (DTH) iminocarbonate), poly(bisphenol A iminocarbonate), poly(ortho ester), polycyanoacrylate, polyphosphazene, modified polysaccharides, modified proteins, and polyurethane.

9. The biocompatible structure of claim 7, further comprising an active material, wherein the active material comprises drugs, and/or cells.

10. The method of claim 2, wherein the modified polysaccharides comprise cellulose, chitin, or dextran, and the modified proteins comprise fibrin, or casein.

11. The biocompatible structure of claim 8, wherein the modified polysaccharides comprise cellulose, chitin, or dextran, and the modified proteins comprise fibrin, or casein.

12. The method of claim 1, wherein the second particles further comprise at least one of gold, silver, cobalt, graphene, calcium phosphate, and ceramic particles.

13. The biocompatible structure of claim 7, wherein the first mixture further comprises at least one of hydroxyapatite with sizes from 1 nm to 100 mm, bone particles with sizes from 1 nm to 100 mm, calcium phosphate powders with sizes from 1 nm to 100 mm, allografts with sizes from 1 nm to 100 mm, and ceramic particles with sizes from 1 nm to 100 mm.

* * * * *